US00PP37626P2

(12) United States Plant Patent
van Swieten

(10) Patent No.: US PP37,626 P2
(45) Date of Patent: Aug. 18, 2026

(54) ***PHALAENOPSIS* PLANT NAMED 'PHA973648'**

(50) Latin Name: *Phalaenopsis hybrida*
Varietal Denomination: PHA973648

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/318,788

(22) Filed: Sep. 4, 2025

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phalaenopsis* plant named 'PHA973648', characterized by its upright plant habit; moderately vigorous growth habit and moderate growth rate; strong flowering stems; freely flowering habit with typically two inflorescences developing per plant, each inflorescence with numerous flowers; dark red-colored flowers with reddish purple-colored labella; and good postproduction longevity.

2 Drawing Sheets

Figure 1:
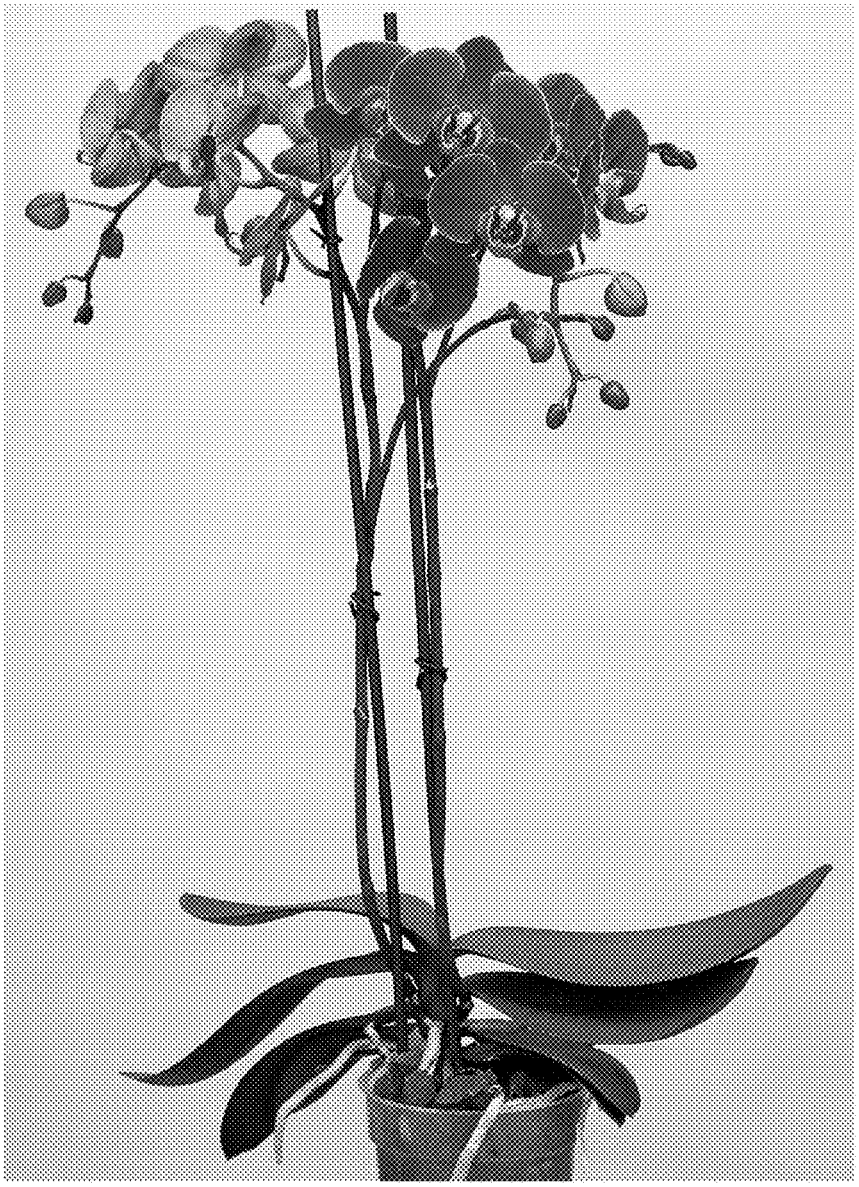

Botanical designation: *Phalaenopsis hybrida.*
Cultivar denomination: 'PHA973648'.

STATEMENT REGARDING PRIOR DISCLOSURES BY INVENTOR and APPLICANT/ASSIGNEE

A European Community Plant Breeder's Rights application for the instant plant was filed by the Applicant/Assignee of the instant application, Anthura B.V. of Bleiswijk, The Netherlands on Aug. 14, 2024, application number 2024/1902. Foreign priority is not claimed to this application.

BACKGROUND OF THE INVENTION

The present invention relates to a new and distinct cultivar of *Phalaenopsis* plant, botanically known as *Phalaenopsis hybrida,* commonly referred to as a *Phalaenopsis* or Moth Orchid and hereinafter referred to by the name 'PHA973648'.

The new *Phalaenopsis* plant is a product of a planned breeding program conducted by the Inventor in Bleiswijk, The Netherlands. The objective of the breeding program is to develop new freely flowering *Phalaenopsis* plants with flowers with unique patterns and coloration.

The new *Phalaenopsis* plant originated from a cross-pollination in September 2017 in Bleiswijk, The Netherlands of a proprietary breeding selection of *Phalaenopsis hybrida* identified as code number 12-051864-0001, not patented, as the female, or seed, parent with *Phalaenopsis hybrida* 'PHALIPZYL', disclosed in U.S. Plant Pat. No. 33,294, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in June 2020.

Asexual reproduction of the new *Phalaenopsis* plant by in vitro meristem propagation in a controlled environment in Bleiswijk, The Netherlands since June 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA973648'. These characteristics in combination distinguish 'PHA973648' as a new and distinct *Phalaenopsis* plant:

1. Upright plant habit.
2. Moderately vigorous growth habit and moderate growth rate.
3. Strong flowering stems.
4. Freely flowering habit with typically two inflorescences developing per plant, each inflorescence with numerous flowers.
5. Dark red-colored flowers with reddish purple-colored labella.
6. Good postproduction longevity.

Plants of the new *Phalaenopsis* can be compared to plants of the female parent selection. Plants of the new *Phalaenopsis* differ primarily from plants of the female parent selection in the following characteristics:

1. Leaves of plants of the new *Phalaenopsis* are horizontal to semi-drooping in aspect whereas leaves of plants of the female parent selection are semi-erect in aspect.

2. The central lobes of the labella of plants of the new *Phalaenopsis* are narrowly deltoid in shape whereas the central lobes of the labella of plants of the female parent selection are trullate in shape.

Plants of the new *Phalaenopsis* can be compared to plants of the male parent, 'PHALIPZYL'. Plants of the new *Phalaenopsis* differ primarily from plants of 'PHALIPZYL' in the following characteristics:

1. Plants of the new *Phalaenopsis* are taller than plants of 'PHALIPZYL'.
2. Flowers of plants of the new *Phalaenopsis* are broader than flowers of plants of 'PHALIPZYL'.
3. Flowers of plants of the new *Phalaenopsis* are flat in lateral view whereas flowers of plants of 'PHALIPZYL' are convex in lateral view.

Plants of the new *Phalaenopsis* can be compared to plants of *Phalaenopsis hybrida* 'PHALFENCK', disclosed in U.S. Plant Pat. No. 27,460. In side-by-side comparisons, plants of the new *Phalaenopsis* differ primarily from plants of 'PHALFENCK' in the following characteristics:

1. Flowers of plants of the new *Phalaenopsis* are dark red in color whereas flowers of plants of 'PHALFENCK' are purple in color.
2. Flower petals of plants of the new *Phalaenopsis* do not have any spots whereas flower petals of plants of 'PHALFENCK' have a few spots.
3. The labella of plants of the new *Phalaenopsis* do not have any stripes whereas the labella of plants of 'PHALFENCK' are striped.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA973648' grown in a container.

Figure 2:
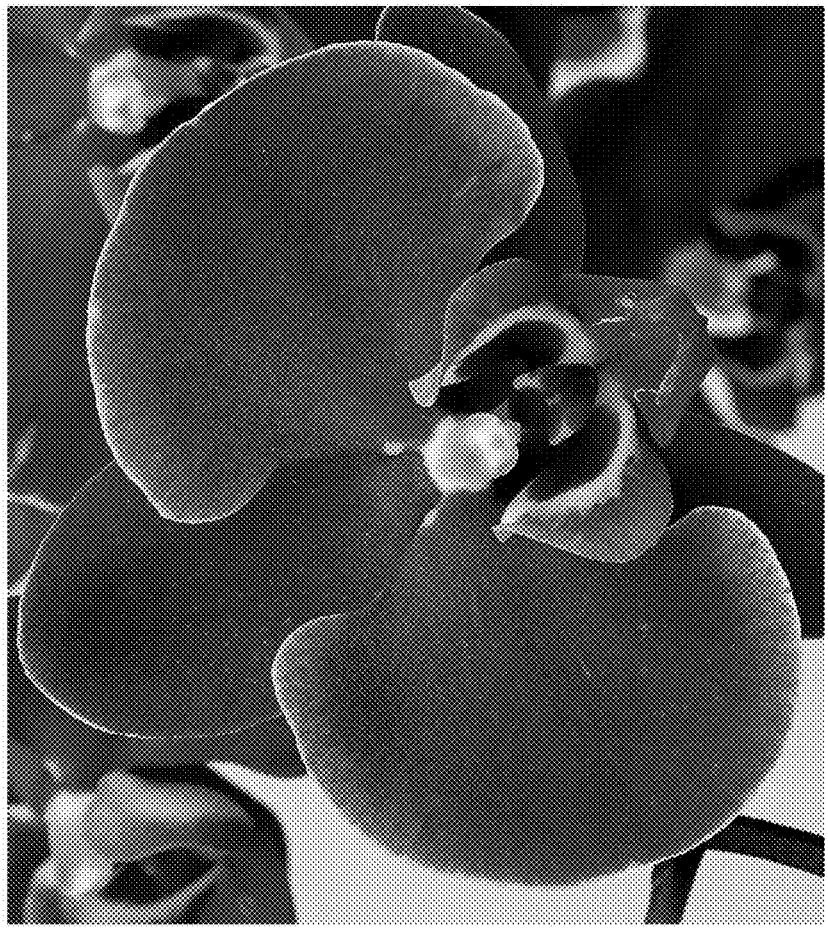

The photograph on the second sheet (FIG. 2) is a close-up view of a typical flower of 'PHA973648'.

DETAILED BOTANICAL DESCRIPTION

The aforementioned photographs and following observations and measurements describe plants grown during the winter and early spring in 12-cm containers in a glass-covered greenhouse in Bleiswijk, The Netherlands and grown under cultural practices typically used in commercial *Phalaenopsis* production. Plants were 18 months old when the photographs and description were taken. During the first 14 months of production of the plants, day and night temperatures averaged 28.5° C., and during the last four months of production of the plants, day and night temperatures averaged 20° C. Throughout the production of the plants, light levels ranged from 100μmol to 180μmol. In the following description, color references are made to The Royal Horticultural Society Colour Chart, 2015 Edition, except where general terms of ordinary dictionary significance are used.

Botanical classification: *Phalaenopsis hybrida* 'PHA973648'.

Parentage:

*Female, or seed, parent.*—Proprietary breeding selection of *Phalaenopsis hybrida* identified as code number 12-051864-0001, not patented.

*Male, or pollen, parent.*—*Phalaenopsis hybrida* 'PHALIPZYL', disclosed in U.S. Plant Pat. No. 33,294.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically light green in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane.*—About 13.2 cm.

*Plant height, substrate level to top of floral plane.*—About 50.9 cm.

*Plant diameter or spread.*—About 32.9 cm.

Leaf description:

*Arrangement and quantity.*—Distichous, simple; sessile; about five to seven fully-developed leaves per plant.

*Length.*—About 19.3 cm.

*Width.*—About 7.1 cm.

*Aspect.*—Horizontal to semi-drooping.

*Shape.*—Obovate to oblanceolate; slightly carinate.

*Apex.*—Unequal and broadly obtuse.

*Base.*—Sheathing. Sheath length: About 1.8 cm. Sheath width: About 1.3 cm. Sheath color: Close to a blend of 148A and 197A tinged with close to N77A.

*Margin.*—Entire; not undulate.

*Texture and luster, upper surface.*—Smooth, glabrous; matte to slightly glossy.

*Texture and luster, lower surface.*—Smooth, glabrous; slightly to moderately glossy.

*Venation pattern.*—Camptodromous.

*Color.*—Developing leaves, upper surface: Close to NN137A tinged with close to N189A; narrow marginal edges, close to N186C. Developing leaves, lower surface: Close to NN137C strongly tinged with close to N186C; narrow marginal edges, close to a blend of N186B and N186C. Fully expanded leaves, upper surface: Close to NN137A; narrow marginal edges, close to N186C; venation, close to N189A. Fully expanded leaves, lower surface: Close to 137C strongly tinged with close to N186C; narrow marginal edges, close to N186C; venation, close to N187A.

Inflorescence description:

*Appearance and flowering habit.*—Showy zygomorphic flowers arranged on axillary simple or branched racemes; typically two inflorescences develop per plant; each inflorescence with about 15 flowers;

flowers face outwardly on upright to outwardly arching inflorescences supported by upright peduncles; flowers with three petals, two lateral petals and one center petal transformed into a labellum and three sepals.

*Fragrance*.—None detected.

*Time to flower*.—Plants begin flowering about five months after planting; plants flower naturally during the winter into the spring.

*Flower longevity*.—Long flowering period, individual inflorescences maintain good substance for about twelve weeks on the plant; flowers not persistent.

*Inflorescence length* (*lowermost flower to inflorescence apex*).—About 31.8 cm.

*Inflorescence width*.—About 16.7 cm.

*Flower buds*.—Height: About 2.1 cm. Diameter: About 1.6 cm by 1.8 cm. Shape: Broadly ovate. Color: Close to N148B and N148C; towards the apex, close to N79C; venation, close to N77A.

*Flower size*.—About 7.2 cm (vertical) by 7.6 cm (horizontal).

*Flower depth*.—About 3.2 cm.

*Petals, quantity and arrangement*.—Three, two lateral petals and one center petal transformed into a labellum.

*Lateral petals*.—Length: About 3.6 cm. Width: About 4.5 cm. Shape: Broadly reniform. Apex: Obtuse. Margin: Entire; not undulate. Texture and luster, upper surface: Smooth, glabrous; velvety; matte. Texture and luster, lower surface: Smooth, glabrous; slightly velvety; matte. Color: When opening, upper surface: Close to 59A; narrow marginal edges, close to 76A; two small dots at base, close to 76A. When opening, lower surface: Close to 76A; towards the apex and margins, close to N77B and N77D; basal margins, close to 76D. Fully opened, upper surface: Close to 59A; towards the apex and margins, close to 72B; narrow marginal edges, close to 76A; two small dots at base, close to 76A; colors do not change with subsequent development. Fully opened, lower surface: Close to a blend of 76A and 76B; towards the apex and margins, close to 77B; narrow marginal edges, close to 76D; colors do not change with subsequent development.

*Labella*.—Appearance: Three-parted with two lateral lobes and a central lobe; overall shape, broadly cordate. Length, lateral lobes: About 2 cm. Width, lateral lobes: About 1.5 cm. Length, central lobe: About 1.8 cm. Width, central lobe: About 6 mm to 16 mm. Length, cirrhose tips: About 1.5 cm. Shape, lateral lobes: Obovate. Shape, central lobe: Narrowly deltoid with a slightly elongated apex. Apex, lateral lobes: Obtuse. Apex, central lobe: Cleft with two cirrhose apices, curled and pointing upwards and backwards. Margins, lateral and central lobes: Entire. Texture and luster, lateral and central lobes, upper and lower surfaces: Smooth, glabrous; velvety; matte. Callosities: Located at the base of the labellum and attachment point of the lateral petals; about 5 mm in length, about 6 mm in width and about 5 mm in height. Color: When opening, upper surface: Lateral lobes: Upper half, close to N78C and N78D with dense venation, close to N79C and N79D; lower half, close to 155A with large blotch, close to 187A and 187B. Central lobe: Close to NN78B; towards the base, close to 71A; at the base close to N186C and N155A; cirrhose apices, close to NN78B blotched with close to 76A. Callosities: Close to 4C and 4D; at the apex, close to N186C and 4B. When opening, lower surface: Lateral lobes: Close to 156D; towards the apex, close to N78A and N78B; basal margins, close to N79C; at the base, close to N187D. Central lobe: Close to N78B; towards the apex, close to N78A; towards the base, close to 71A and at the base close to 156D; cirrhose apices, close to N78A blotched with close to 76A. Fully opened, upper surface: Lateral lobes: Upper half, close to N78C and N78D with dense venation, close to N79C and N79D; lower half, close to NN155C with large blotch, close to 187A and 187B. Central lobe: Close to NN78B; towards the base, close to 71A; at the base close to N186C and N155A; cirrhose apices, close to NN78B blotched with close to 76A. Callosities: Close to 4C; at the apex, close to N186C and 7C. Fully opened, lower surface: Lateral lobes: Close to 156D; towards the apex, close to N78A and N78B; basal margins, close to N79C; at the base, close to N187D. Central lobe: Close to N78B; towards the apex, close to N78A; towards the base, close to 71A and at the base close to 156D; cirrhose apices, close to N78A blotched with close to 76A.

*Sepals*.—Quantity and arrangement: Three, one upper dorsal sepal and two lower lateral sepals. Length, dorsal sepal: About 3.9 cm. Width, dorsal sepal: About 2.6 cm. Length, lateral sepals: About 3.8 cm. Width, lateral sepals: About 2.3 cm. Shape, dorsal sepal: Obovate-oblong. Shape, lateral sepals: Ovate. Apex, dorsal and lateral sepals: Bluntly acute. Base, dorsal and lateral sepals: Cuneate. Margins, dorsal and lateral sepals: Entire; not undulate. Texture and luster, dorsal and lateral sepals, upper and lower surfaces: Smooth, glabrous; moderately velvety; matte. Color, dorsal sepal: When opening, upper surface: Close to 59B; narrow marginal edges, close to 76A; venation, close to 187A. When opening, lower surface: Close to 186C; broad apical margins, close to N78C; central blotch, close to 64A; venation, close to 64A. Fully opened, upper surface: Close to 59A and 59B; narrow marginal edges, close to 76A; venation, close to 187A. Fully opened, lower surface: Close to 75A; broad apical margins, close to N78C; central blotch, close to 71A; venation, close to 71A. Color, lateral sepals: When opening, upper surface: Close to 59A; venation, close to 187A. When opening, lower surface: Close to 186C; towards the base, tinged with close to N148A and N148B; venation, close to 61A. Fully opened, upper surface: Close to 59A and 59B; narrow marginal edges, close to 76A; venation, close to 187A. Fully opened, lower surface: Close to N75A; towards the apex, close to 71A; towards the base, tinged with close to N148D; venation, close to 71A.

*Peduncles*.—Length: About 59.1 cm. Diameter: About 6 mm. Strength: Strong. Aspect: Upright to outwardly arching. Texture and luster: Smooth, glabrous; matte. Color: Close to a blend of 200A and 200B with dense fine dots, close to 147C.

*Pedicels*.—Length: About 3.8 cm. Diameter: About 3 mm. Strength: Moderately strong. Aspect: About 55° from peduncle axis. Texture and luster: Smooth, glabrous; matte. Color: Close to N148B; distal end, close to 186D; proximal end, close to N199A.

*Reproductive organs*.—Androecium: Column length: About 9 mm. Column width: About 5 mm. Column color: Close to N78B and N78C; at the base, close to NN155D. Pollinia quantity: Two. Pollinia diameter (per two pollinia): About 2 mm. Pollinia color: Close to 21A. Gynoecium: Stigma length: About 4 mm. Stigma width: About 4 mm. Stigma shape: Reniform. Stigma color: Close to N155C. Ovary length: About 8 mm. Ovary diameter: About 1 mm. Ovary color: Close to 149C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA973648' as herein illustrated and described.

* * * * *